US00PP37677P2

(12) United States Plant Patent
Mathey

(10) Patent No.: US PP37,677 P2
(45) Date of Patent: Sep. 8, 2026

(54) ***DEUTZIA* PLANT NAMED 'SMNDXI'**

(50) Latin Name: ***Deutzia* sp.**
Varietal Denomination: SMNDXI

(71) Applicant: Megan M. Mathey, Holland, MI (US)

(72) Inventor: Megan M. Mathey, Holland, MI (US)

(73) Assignee: SPRING MEADOW NURSERY, INC., Grand Haven, MI (US)

( * ) Notice: Subject to any disclaimer, the term of this patent is extended or adjusted under 35 U.S.C. 154(b) by 0 days.

(21) Appl. No.: 19/383,646

(22) Filed: Nov. 8, 2025

(51) Int. Cl.
*A01H 5/00* (2018.01)
*A01H 6/48* (2018.01)

(52) U.S. Cl.
USPC ..... Plt./226

(58) Field of Classification Search
USPC ..... Plt./226
See application file for complete search history.

(56) References Cited

U.S. PATENT DOCUMENTS

PP36,667 P2 * 5/2025 Ranney ..... Plt./226

* cited by examiner

*Primary Examiner* — Susan Mccormick Ewoldt
*Assistant Examiner* — Zachariah Allan Kay
(74) *Attorney, Agent, or Firm* — C. Anne Whealy

(57) ABSTRACT

A new and distinct cultivar of *Deutzia* plant named 'SMNDXI', characterized by its compact, upright to outwardly spreading and low, uniformly mounding plant habit; vigorous growth habit; freely branching habit; dense and bushy habit; leaves that become dark red to reddish brown in the autumn and under conditions of high light and high temperatures; large inflorescences with numerous light purple-colored flower buds and white-colored flowers with a purple-colored stripe on the lower petal surface; and good garden performance.

3 Drawing Sheets

Figure 1:
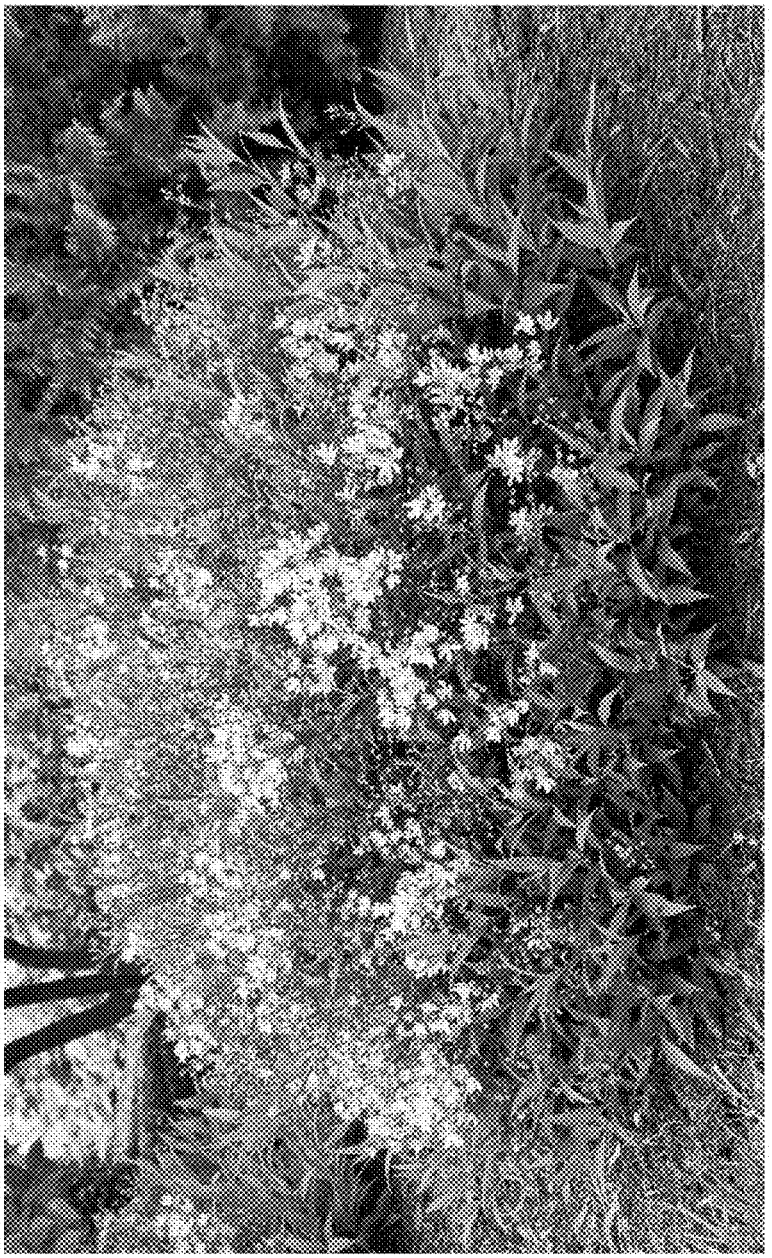

Botanical designation: *Deutzia* sp.
Cultivar denomination: 'SMNDXI'.

BACKGROUND OF THE INVENTION

The present invention relates to a new and distinct cultivar of *Deutzia* plant, botanically known as *Deutzia* sp. and hereinafter referred to by the name 'SMNDXI'.

The new *Deutzia* plant is a product of a planned breeding program conducted by the Inventor in Grand Haven, Michigan. The objective of the breeding program is to develop new compact and mounding *Deutzia* plants with unique leaf and flower coloration.

The new *Deutzia* plant originated from an open-pollination during the summer of 2016 of *Deutzia* sp. 'NCDX2', disclosed in U.S. Plant Pat. No. 28,347, as the female, or seed, parent with an unknown proprietary selection of *Deutzia* sp., as the male, or pollen, parent. The new *Deutzia* plant was discovered and selected by the Inventor as a single flowering plant within the progeny of the stated open-pollination in a controlled environment in Grand Haven, Michigan during the summer of 2021.

Asexual reproduction of the new *Deutzia* plant by softwood cuttings in a controlled greenhouse environment in Grand Haven, Michigan since the summer of 2021 has shown that the unique features of this new *Deutzia* plant are stable and reproduced true to type in successive generations of asexual reproduction.

SUMMARY OF THE INVENTION

Plants of the new *Deutzia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SMNDXI'. These characteristics in combination distinguish 'SMNDXI' as a new and distinct *Deutzia* plant:

1. Compact, upright to outwardly spreading and low, uniformly mounding plant habit.
2. Vigorous growth habit.
3. Freely branching habit; dense and bushy habit.
4. Leaves that become dark red to reddish brown in the autumn and under conditions of high light and high temperatures.
5. Large inflorescences with numerous light purple-colored flower buds and white-colored flowers with a purple-colored stripe on the lower petal surface.
6. Good garden performance.

Plants of the new *Deutzia* can be compared to plants of the female parent, 'NCDX2'. Plants of the new *Deutzia* differ primarily from plants of 'NCDX2' in the following characteristics:

1. Under conditions of high light and high temperatures, leaves of plants of the new *Deutzia* become dark red to reddish brown in color whereas leaves of plants of 'NCDX2' are consistently green in color.
2. Flower buds of plants of the new *Deutzia* are darker purple in color than flower buds of plants of 'NCDX2'.
3. The stripe on the lower petal surface of plants of the new *Deutzia* is darker purple in color than the stripe on the lower petal surface of plants of 'NCDX2'.

Plants of the new *Deutzia* can be compared to plants of the *Deutzia* sp. 'NCDX3', disclosed in U.S. Plant Pat. No. 36,667. Plants of the new *Deutzia* differ from plants of 'NCDX3' in the following characteristics:

1. Under conditions of high light and high temperatures, leaves of plants of the new *Deutzia* become dark red to reddish brown in color whereas leaves of plants of 'NCDX3' are consistently green in color.
2. Flowers of plants of the new *Deutzia* are smaller than flowers of plants of 'NCDX3'.
3. The stripe on the lower petal surface of plants of the new *Deutzia* is lighter purple in color than the stripe on the lower petal surface of plants of 'NCDX3'.

BRIEF DESCRIPTION OF THE PHOTOGRAPHS

The accompanying colored photographs illustrate the overall appearance of the new *Deutzia* plant showing the colors as true as it is reasonably possible to obtain in colored reproductions of this type. Colors in the photographs may differ slightly from the color values cited in the detailed botanical description which accurately describe the colors of the new *Deutzia* plant.

The photograph on the first sheet (FIG. 1) is a side perspective view of a typical plant of 'SMNDXI' grown in an outdoor nursery.

Figure 2:
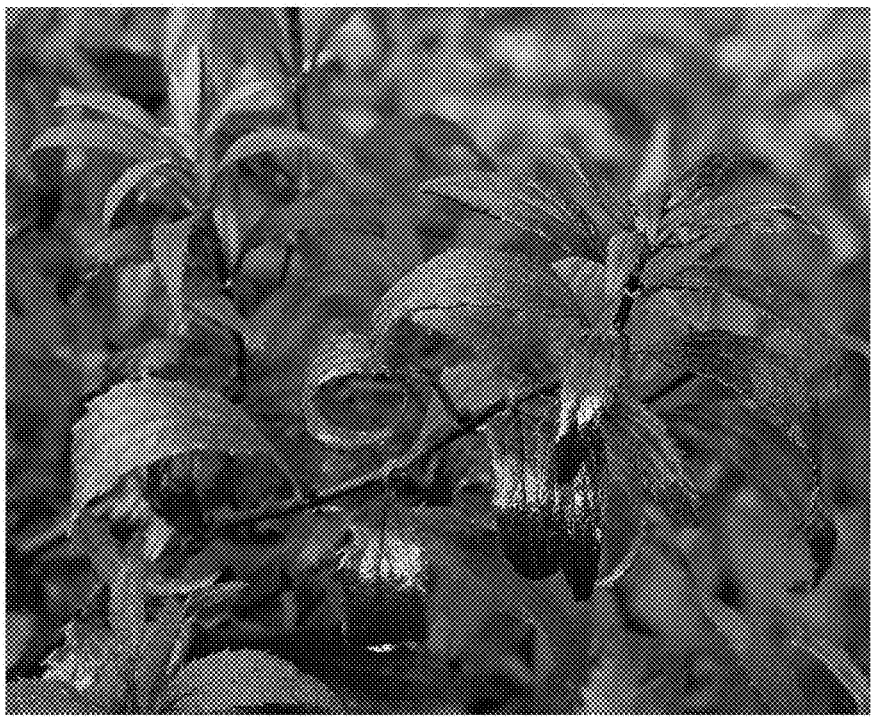

The photograph on the second sheet (FIG. 2) is a close-up view of typical leaves of 'SMNDXI' during the autumn grown in an outdoor nursery.

Figure 3:
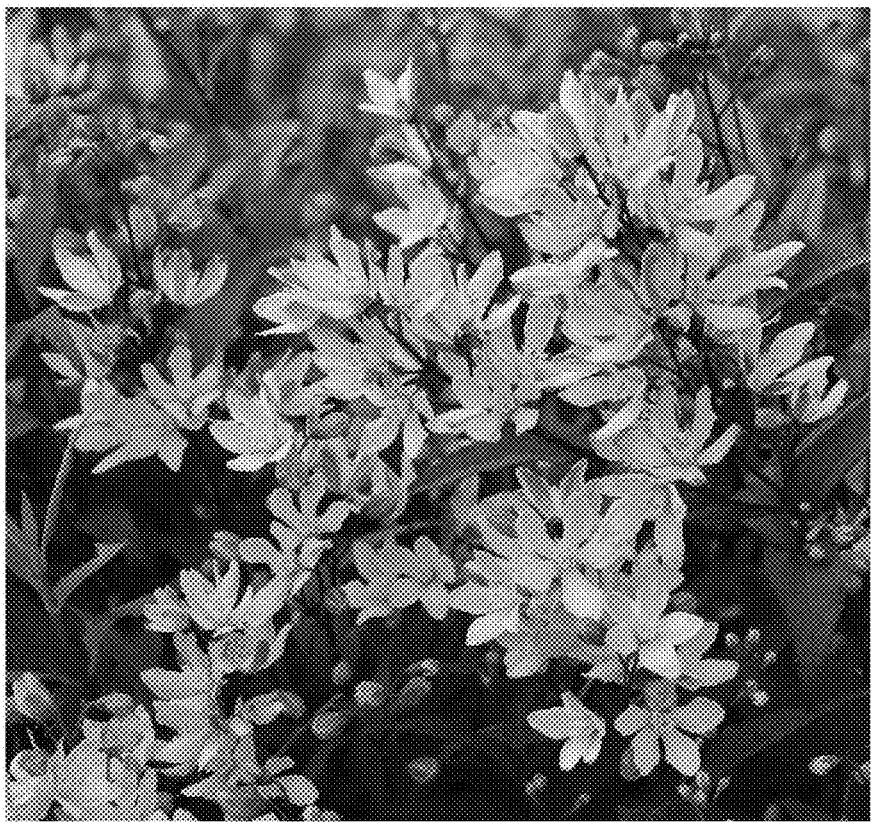

The photograph on the third sheet (FIG. 3) is a close-up view of typical flowers of 'SMNDXI' grown in an outdoor nursery.

Plants used in the photographs were grown during the summer and autumn in Grand Haven, Michigan and were three years old.

DETAILED BOTANICAL DESCRIPTION

The following observations and measurements describe plants grown during the spring in three-gallon containers in a polyethylene-covered greenhouse in Grand Haven, Michigan and under cultural practices typical of commercial *Deutzia* production. During the production of the plants, day temperatures ranged from 18° C. to 27° C. and night temperatures ranged from ranged from 5° C. to 10° C. Plants were three years old when the detailed description were taken. In the following description, color references are made to The Royal Horticultural Society Colour Chart, 2015 Edition, except where general terms of ordinary dictionary significance are used.

Botanical classification: *Deutzia* sp. 'SMNDXI'.

Parentage:

*Female, or seed, parent.*—*Deutzia* sp. 'NCDX2', disclosed in U.S. U.S. Plant Pat. No. 28,347.

*Male, or pollen, parent.*—Unknown proprietary selection of *Deutzia* sp., not patented.

Propagation:

*Type.*—By softwood cuttings.

*Time to initiate roots, summer.*—About twelve days at temperatures about 18° C. to 27° C.

*Time to produce a rooted young plant, summer.*—About 20 days at temperatures about 18° C. to 27° C.

*Root description.*—Medium in thickness; fibrous; typically off-white to beige in color, actual color of the roots is dependent on substrate composition, water quality, fertilizer, substrate temperature and physiological age of roots.

*Rooting habit.*—Moderately freely branching; medium density.

Plant description:

*Plant form and growth habit.*—Perennial shrub; compact, upright to outwardly spreading and low, uniformly mounding plant habit; overall plant shape, rounded; vigorous growth habit and moderate growth rate; large and dense inflorescences positioned just above the foliar plane; plants grown under greenhouse conditions will be more upright than and not as spreading as outdoor nursery-grown plants.

*Plant height, soil level to top of foliar plane.*—About 70 cm.

*Plant height, soil level to top of floral plane.*—About 75 cm.

*Plant diameter* (*area of spread*).—About 35 cm.

Lateral branch description:

*Branching habit.*—Freely branching habit with about seven to ten primary lateral branches each with about eight secondary lateral branches developing per plant; tightly branched, dense and bushy habit.

*Length, primary lateral branches.*—About 35 cm.

*Diameter, primary lateral branches.*—About 4 mm.

*Internode length.*—About 4 cm.

*Strength.*—Moderately strong.

*Aspect.*—About 20° to 45° from vertical.

*Texture and luster.*—Smooth, glabrous; becoming woody with development; matte.

*Color, developing.*—Close to between 176A and 166A.

*Color, developed.*—Close to 165A; if woody, close to 200A.

Leaf description:

*Arrangement.*—Opposite; simple.

*Length.*—About 4.5 cm.

*Width.*—About 1.25 cm.

*Shape.*—Lanceolate.

*Apex.*—Acute.

*Base.*—Cuneate.

*Margin.*—Serrate.

*Texture and luster, upper and lower surfaces.*—Smooth, glabrous; matte.

*Venation pattern.*—Pinnate.

*Color.*—Developing and fully expanded leaves, upper surface: Close to between 146A and NN137B; venation, close to 146B, towards the base, tinged with close to 177A; in the autumn and under conditions of high light and high temperatures, color becoming closer to between 187A and 200A. Developing and fully expanded leaves, lower surface: Close to 146B; venation, close to 146B; in the autumn and under conditions of high light and high temperatures, color becoming closer to between 187A and 200A.

*Petioles.*—Length: About 4 mm. Diameter: About 2 mm. Texture and luster, upper and lower surfaces: Smooth, glabrous; semi-glossy. Color, upper and lower surfaces: Close to 177A.

Flower description:

*Flower appearance and arrangement.*—Single rotate flowers arranged in terminal and axillary panicles; freely flowering habit, per plant with about 15 to 20 flowers per inflorescence and about 1,000 flowers developing per plant during the flowering season; flowers face upright to outwardly depending on position on inflorescence.

*Natural flowering season*.—Continuous flowering during the spring (April through May) in Michigan.

*Flower longevity*.—Depending on temperature, individual flowers last about one week; flowers not persistent.

*Fragrance*.—None detected.

*Inflorescence height*.—About 10 cm.

*Inflorescence diameter*.—About 5.5 cm.

*Flower size*.—About 1 cm by 2 cm.

*Flower depth*.—About 2 cm.

*Flower buds*.—Length: About 5 mm. Diameter: About 3 mm. Shape: Ovoid. Texture and luster: Smooth, glabrous; matte. Color: Close to 75A.

*Petals*.—Quantity and arrangement: Five in a single whorl. Length: About 1.2 cm. Width: About 7 mm. Shape: Elliptic. Apex: Broadly acute. Base: Cuneate. Margin: Entire; slightly undulate. Texture and luster, upper and lower surfaces: Smooth, glabrous; silky; matte. Color: When opening, upper surface: Close to NN155C. When opening, lower surface: Close to NN155C with a medial stripe (3 mm in width), close to 75A. Fully opened, upper surface: Close to NN155C; color does not change with subsequent development. Fully opened, lower surface: Close to NN155C with a medial stripe (3 mm in width), close to 75B; color does not change with subsequent development.

*Sepals*.—Quantity and arrangement: Five in a single whorl; fused at the base. Length: About 3 mm. Width: About 1.5 mm. Shape: Deltoid. Apex: Acute. Margin: Entire. Texture and luster, upper and lower surfaces: Smooth, glabrous; matte. Color: When opening, upper and lower surfaces: Close to 145C; at the apex, tinged with close to 176A. Fully opened, upper and lower surfaces: Close to 145C; at the apex, tinged with close to 176A.

*Peduncles*.—Length: About 9 cm. Diameter: About 2 mm. Strength: Moderately strong. Aspect: Mostly erect. Texture and luster: Smooth, glabrous; matte. Color: Close to 178A.

*Pedicels*.—Length: About 1 cm. Diameter: About 1 mm. Strength: Moderately strong. Aspect: About 45° from peduncle axis. Texture and luster: Smooth, glabrous; matte. Color: Close to 178A.

*Reproductive organs*.—Androecium: Quantity per flower: About ten. Filament length: About 5 mm. Filament color: Close to NN155C. Anther shape: Globose. Anther size: About 1 mm by 1 mm. Anther color: Close to 7A. Amount of pollen: Moderate. Pollen color: Close to 7A. Gynoecium: Quantity per flower: About three. Pistil length: About 7 mm. Style length: About 6 mm. Style color: Close to 8D. Stigma diameter: About 0.5 mm. Stigma shape: Rounded. Stigma color: Close to 4D. Ovary color: Close to 144B.

*Seeds and fruits*.—To date, seed and fruit development has not been observed on plants of the new *Deutzia*.

Garden performance: Plants of the new *Deutzia* have been observed to have good garden performance and to tolerate rain, wind and to be suitable for USDA Hardiness Zones 5a to 8b.

Pathogen & pest resistance: To date, plants of the new *Deutzia* have not been observed to be resistant to pathogens and pests common to *Deutzia* plants.

It is claimed:

1. A new and distinct *Deutzia* plant named 'SMNDXI' as herein illustrated and described.

* * * * *